US012797048B2

(12) United States Patent
Kamolz

(10) Patent No.: US 12,797,048 B2
(45) Date of Patent: Nov. 17, 2026

(54) APPARATUS FOR AND METHOD OF OBTAINING A BIOLOGICAL SAMPLE FROM A SURFACE

(71) Applicant: Cerdak (Pty) Ltd, Mtunzini (ZA)

(72) Inventor: Lars-Peter Kamolz, Hart bei Graz (AT)

(73) Assignee: CERDAK (PTY) LTD, Mtunzini (ZA)

( * ) Notice: Subject to any disclaimer, the term of this patent is extended or adjusted under 35 U.S.C. 154(b) by 382 days.

(21) Appl. No.: 18/555,065

(22) PCT Filed: Apr. 20, 2022

(86) PCT No.: PCT/IB2022/053674
§ 371 (c)(1),
(2) Date: Oct. 12, 2023

(87) PCT Pub. No.: WO2022/224152
PCT Pub. Date: Oct. 27, 2022

(65) Prior Publication Data

US 2024/0188941 A1 Jun. 13, 2024

(30) Foreign Application Priority Data

Apr. 20, 2021 (ZA) .................................. 202102598

(51) Int. Cl.

| | |
|---|---|
| ***A61B 5/00*** | (2006.01) |
| ***A61B 10/00*** | (2006.01) |
| ***A61F 13/36*** | (2006.01) |
| ***A61L 15/18*** | (2006.01) |
| ***A61L 15/42*** | (2006.01) |
| ***C12N 13/00*** | (2006.01) |
| ***C12Q 1/04*** | (2006.01) |
| *A61F 13/15* | (2006.01) |

(52) U.S. Cl.
CPC .......... *A61B 10/0045* (2013.01); *A61F 13/36* (2013.01); *A61L 15/18* (2013.01); *A61L 15/425* (2013.01); *C12N 13/00* (2013.01); *C12Q 1/04* (2013.01); *A61F 2013/15365* (2013.01)

(58) Field of Classification Search
CPC ........... A61B 10/0045; A61B 2010/008; A61F 13/36; A61F 2013/15365; A61L 15/18; A61L 15/425; C12N 13/00; C12Q 1/04
See application file for complete search history.

(56) References Cited

U.S. PATENT DOCUMENTS 9,574,245 B2 * 2/2017 Talebpour ......... B01L 3/502738
2002/0072702 A1 * 6/2002 Quay ...................... A61M 1/06 604/74
2004/0193030 A1 9/2004 Aston et al.
2014/0018701 A1 * 1/2014 Mao .................... H01J 49/0436 600/583
2014/0206060 A1 * 7/2014 Halaka .................... B02C 19/18 435/306.1
2014/0271757 A1 * 9/2014 Agrawal .................. C09D 5/14 507/90
2015/0079655 A1 * 3/2015 Laugharn, Jr. ........... G01N 1/34 435/306.1
2015/0259722 A1 * 9/2015 Awdeh .................. B65D 25/04 435/288.7
2016/0166185 A1 * 6/2016 Liepmann ........ A61B 5/150503 600/365
2016/0220728 A1 * 8/2016 Adams ..................... A61K 8/20
2017/0304485 A1 * 10/2017 Kshirsagar .............. A61P 17/02
2017/0367895 A1 * 12/2017 Holm ...................... A61P 17/02
2018/0252701 A1 * 9/2018 Rhodes .................. G01N 21/78
2019/0241936 A1 * 8/2019 Liu ...................... C12Q 1/6895
2020/0030480 A1 * 1/2020 Choi ....................... A61L 15/44
2020/0147258 A1 * 5/2020 Galabura .............. A61F 13/537
2020/0289049 A1 * 9/2020 Rozand ................ A61B 5/6832
2021/0102187 A1 * 4/2021 Vivek .................... C12N 13/00
2021/0115406 A1 * 4/2021 Kerns .................... C12M 35/04
2021/0311028 A1 * 10/2021 Kornberg ............. G01N 33/532
2021/0322622 A1 * 10/2021 Miller ................... A61K 38/14
2021/0338486 A1 * 11/2021 Dagger .................... A61N 7/00
2022/0142830 A1 * 5/2022 Lambertz ............. A61L 15/225
2022/0229065 A1 * 7/2022 Rai .......................... C12Q 1/44
2022/0241454 A1 * 8/2022 Lang ....................... A61L 15/24
2022/0313129 A1 * 10/2022 Barone .............. A61B 5/15113
2022/0340951 A1 * 10/2022 Corrigan .............. G01N 27/122
2022/0362060 A1 * 11/2022 Rehbein ............. A61F 13/0246
2023/0046062 A1 * 2/2023 Dutta ...................... A61L 15/44
2023/0151386 A1 * 5/2023 Henry .................. A61N 5/0624 424/93.2
2023/0175034 A1 * 6/2023 Marcoux ................ G01N 21/03 435/34

FOREIGN PATENT DOCUMENTS

EP 2523605 A1 11/2012
GB 2506010 A 3/2014
RU 2615075 C2 * 4/2017 ....... A61F 13/00055
TW 200300666 A * 6/2003

OTHER PUBLICATIONS

International Search Report issued in International Application No. PCT/IB2022/053674 on Jul. 8, 2022 (5 pages).
Written Opinion issued in International Application No. PCT/IB2022/053674 on Jul. 8, 2022 (7 pages).

* cited by examiner

*Primary Examiner* — May A Abouelela
(74) *Attorney, Agent, or Firm* — McNeill PLLC

(57) ABSTRACT

An apparatus for obtaining a biological sample from an exposed surface of a human or animal body, the apparatus including a plurality of separate and porous ceramic particles for absorbing and adsorbing biological material from the exposed surface; and a permeable covering for containing the plurality of separate and porous ceramic particles, wherein the biological material having been absorbed and adsorbed by the plurality of separate and porous ceramic particles forms the biological sample.

11 Claims, 2 Drawing Sheets

APPARATUS FOR AND METHOD OF OBTAINING A BIOLOGICAL SAMPLE FROM A SURFACE

CROSS-REFERENCE TO RELATED APPLICATIONS

This application is a national phase entry pursuant to 35 U.S.C. § 371 of International Application No. PCT/IB2022/053674, filed Apr. 20, 2022, which claims the benefit of priority to South African Application No. 2021/02598, filed Apr. 20, 2021.

FIELD OF THE INVENTION

The invention pertains to an apparatus for and a method of obtaining a biological sample from a surface. More particularly, the invention pertains to an apparatus for and a method of obtaining a biological sample from an exposed surface of a human or animal body.

BACKGROUND TO THE INVENTION

Infection of acute and chronic wounds presents a major impairment to wound healing. Most infected wounds are caused by bacterial colonization, originating either from the normal flora on the skin, or bacteria from other parts of the body or the outside environment.

In order to prescribe the correct treatment for the infected wound, a proper diagnostic assessment has to be performed. The diagnostic assessment is necessary to identify the causative organism (e.g., bacteria) of the infection.

It is known to analyse wound exudate to predict wound healing and to guide wound care. However, currently no biological assay exists to objectively assess wounds to aid in timing of wound closure and guide therapy. Changes in levels of proteases, protease inhibitors, and inflammatory markers have been correlated with wound healing. These findings further support the idea that inflammatory dysregulation and a persistent inflammatory state leads to failure of wound healing in the acute setting. These findings highlight potential targets for the development of a biological assay to individualize management of complex soft-tissue wounds, based on patient physiology and response, that would be applicable to not only military trauma but also civilian trauma. Ultimately, this would result in earlier wound closure, reduction in the number of operating room trips, and reduced health care costs. (Hahm, G., Glaser, J J., Elster, E A. (2011) Biomarkers to predict wound healing: the future of complex war wound management. *Plastic Reconstructive Surgery* 127).

A biological marker (biomarker) is a substance used as an indicator of biological state. Advances in genomics, proteomics and molecular pathology have generated many candidate biomarkers with potential clinical value. Research has identified several cellular events and mediators associated with wound healing that can serve as biomarkers. Macrophages, neutrophils, fibroblasts and platelets release cytokines molecules including TNF-α, interleukins (ILs) and growth factors, of which platelet-derived growth factor (PDGF) holds the greatest importance. As a result, various white cells and connective tissue cells release both matrix metalloproteinases (MMPs) and the tissue inhibitors of metalloproteinases (TIMPs). Studies have demonstrated that IL-1, IL-6, and MMPs, levels above normal, and an abnormally high MMP/TIMP ratio are often present in non-healing wounds. Clinical examination of wounds for these mediators could predict which wounds will heal and which will not, suggesting use of these chemicals as biomarkers of wound healing. There is also evidence that the application of growth factors like PDGF will alleviate the recuperating process of chronic, non-healing wounds. Finding a specific biomarker for wound healing status would be a breakthrough in this field and helping treat impaired wound healing. (Patel, S., Maheshwari, A., Chandra, A. (2016); Biomarkers for wound healing and their evaluation—*Wound Care* (1):46-55).

The so-called swab-rinse technique is most often employed for the diagnostic assessment.

Conventional swabs used in the swab-rinse technique are made from a wooden or plastic shaft with cotton fibres spun to form a bud at one end of the shaft. In performing the swab-rinse technique, the bud is rubbed over the surface of the wound so as to remove bacteria. The bud may, optionally, be moistened in an appropriate wetting agent. Bacteria are then removed from the bud and transferred directly to a solid nutrient medium to develop a laboratory culture. The laboratory culture is then used to identify the causative organism.

The effectiveness of the above-described technique depends, amongst other things, on:

(i) the removal of bacteria from the surface of the wound;

(ii) the release of the bacteria from the bud of the swab; and (iii) the cultivation of the bacteria.

The above-described technique works only if the swab was performed properly.

It is known that swabbing efficacy is often poor. Studies have reported bacterial recovery rates ranging from 25% to just 0.1% of the original inoculum (Niskanen and Pohja 1977; Roelofsen et al. 1999; Moore and Griffith 2002; Taku et al. 2002; Obee et al. 2004).

Among the reasons for the poor efficacy of conventional swabbing techniques are inadequate training of a user taking the swab, ineffective absorption and adsorption capability of the bud of the swab and ineffective release of the bacteria from the bud of the swab.

OBJECT OF THE INVENTION

It is an object of the present invention to provide an apparatus for and a method of obtaining a biological sample from an exposed surface of a human or animal body with which the applicant believes the above disadvantages may at least be alleviated or which will provide a useful alternative to known apparatuses and methods.

SUMMARY OF THE INVENTION

An apparatus for obtaining a biological sample from an exposed surface of a human or animal body, the apparatus including:

a plurality of separate and porous ceramic particles for absorbing and adsorbing biological material from the exposed surface; and a permeable covering for containing the plurality of separate and porous ceramic particles, wherein the biological material having been absorbed and adsorbed by the plurality of separate and porous ceramic particles forms the biological sample.

The exposed surface may be a wound of a human or animal. The wound may be infected. The biological material may include the biological material includes wound exudate containing any one or more selected from the group consisting of microorganisms, biomarkers, deoxyribonucleic acid (DNA), proteins, cellular molecules, endotoxins or combinations thereof, macrophages, neutrophils, fibroblasts, platelets, cytokines molecules including TNF-α, interleukins (ILs) and growth factors, including platelet-derived growth factor (PDGF), matrix metalloproteinases (MMPs), tissue inhibitors of metalloproteinases (TIMPs), IL-1, IL-6, and MMPs, proteases, protease inhibitors, and inflammatory markers, and the microorganisms include any one or more selected from the group consisting of bacteria, viruses, fungi and parasites.

The permeable covering may take the form of a permeable and wettable sachet or an envelope. The permeable covering may be formed from an organic, non-woven material. The permeable covering may be a sterile covering.

The plurality of separate and porous ceramic particles may be inert.

The plurality of separate and porous ceramic particles may have a porosity of between 25% and 85%.

The plurality of separate and porous ceramic particles may have pores with a diameter of between 0.3 and 30 micrometres. The pores may be cellular in nature. The pores may be interconnected with one another by means of blow-holes.

The plurality of separate and porous ceramic particles may have a diameter of between 300 and 3000 micrometres.

The plurality of separate and porous ceramic particles may have a charged surface. The charged surface may be caused by ionic and electrostatic interaction, hydrogen bonding and charge-transfer interactions.

According to second aspect of the invention, there is provided for a method of obtaining a biological sample from an exposed surface of a human or animal body, the method including the steps of:

(i) providing the apparatus according to the first aspect of the invention; and (ii) contacting the apparatus with the exposed surface to permit the plurality of separate and porous ceramic particles to absorb and adsorb biological material from the exposed surface, wherein the biological material having been absorbed and adsorbed by the plurality of separate and porous ceramic particles forms the biological sample.

The exposed surface may be a wound of a human or animal. The wound may be infected. The biological material may include wound exudate containing any one or more selected from the group consisting of microorganisms, biomarkers, deoxyribonucleic acid (DNA), proteins, cellular molecules, endotoxins or combinations thereof, macrophages, neutrophils, fibroblasts, platelets, cytokines molecules including TNF-α, interleukins (ILs) and growth factors, including platelet-derived growth factor (PDGF), matrix metalloproteinases (MMPs), tissue inhibitors of metalloproteinases (TIMPs), IL-1, IL-6, and MMPs, proteases, protease inhibitors, and inflammatory markers, and the microorganisms include any one or more selected from the group consisting of bacteria, viruses, fungi and parasites.

According to a third aspect of the invention, there is provided for the use of the apparatus according to the first aspect of the invention to obtain a biological sample from an exposed surface of a human or animal body.

According to a fourth aspect of the invention, there is provided for a diagnostic method, the diagnostic method including the steps of:

(i) providing the apparatus according to the first aspect of the invention;

(ii) contacting the apparatus with the exposed surface to permit the plurality of separate and porous ceramic particles to absorb and adsorb biological material from the exposed surface; and (iii) subjecting the apparatus to sonication to form a sonication fluid, the sonication step serving to disintegrate a biofilm of microorganisms present in the absorbed and adsorbed biological material so as to form a sonication fluid containing microorganisms.

The exposed surface may be a wound of a human or animal. The wound may be infected. The biological material may include wound exudate containing any one or more selected from the group consisting of microorganisms, biomarkers, deoxyribonucleic acid (DNA), proteins, cellular molecules, endotoxins or combinations thereof, macrophages, neutrophils, fibroblasts, platelets, cytokines molecules including TNF-α, interleukins (ILs) and growth factors, including platelet-derived growth factor (PDGF), matrix metalloproteinases (MMPs), tissue inhibitors of metalloproteinases (TIMPs), IL-1, IL-6, and MMPs, proteases, protease inhibitors, and inflammatory markers, and the microorganisms include any one or more selected from the group consisting of bacteria, viruses, fungi and parasites.

Sonication may be performed at frequencies of 20 kilohertz.

The diagnostic method may include the additional step of using the sonication fluid to cultivate a bacterial culture or cultures for identifying bacterial strains present in the sonication fluid.

DETAILED DESCRIPTION OF THE INVENTION

The plurality of separate and porous ceramic particles may be formed by a method including the steps of:

(i) milling alumina ($Al_2O_3$) into a powder consisting of particles having a diameter of approximately 1 micrometre;

(ii) adding a combustible substance to the powder;

(iii) mixing the powder with water to form a paste or slurry;

(iv) forming of particles from paste or slurry to separate particles having a diameter of between 300 and 3000 micrometres; and (v) heating the ceramic aggregate to a temperature of 1200° C., to form an inert microporous solid ceramic body having pore sizes of between 0.3 and 30 micrometres.

Each of the plurality of separate and porous ceramic particles has a diameter of between 30 and 3000 micrometres, are inert and have a porosity of between 25% and 85%.

The pores of the plurality of separate and porous ceramic particles are cellular in nature and have a diameter of between 0.3 and 30 micrometres. The pores are interconnected to one another by means of blow-holes, which form when the combustible substance escapes from the ceramic aggregate when the latter melts at or close to 1200° C.

Figure 1:
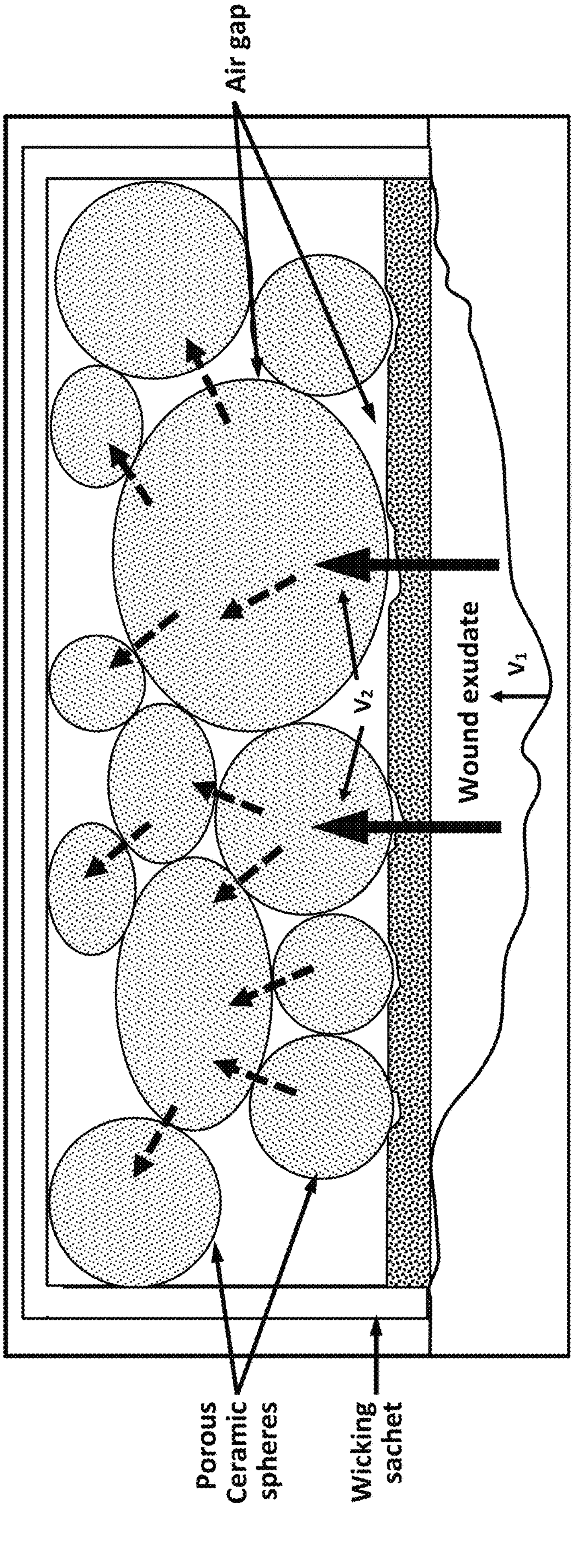
FIG. 1 is a schematic view of an apparatus configured to collect a biological sample from a surface, including a plurality of separate and porous ceramic particles housed within a sachet.
Figure 2:
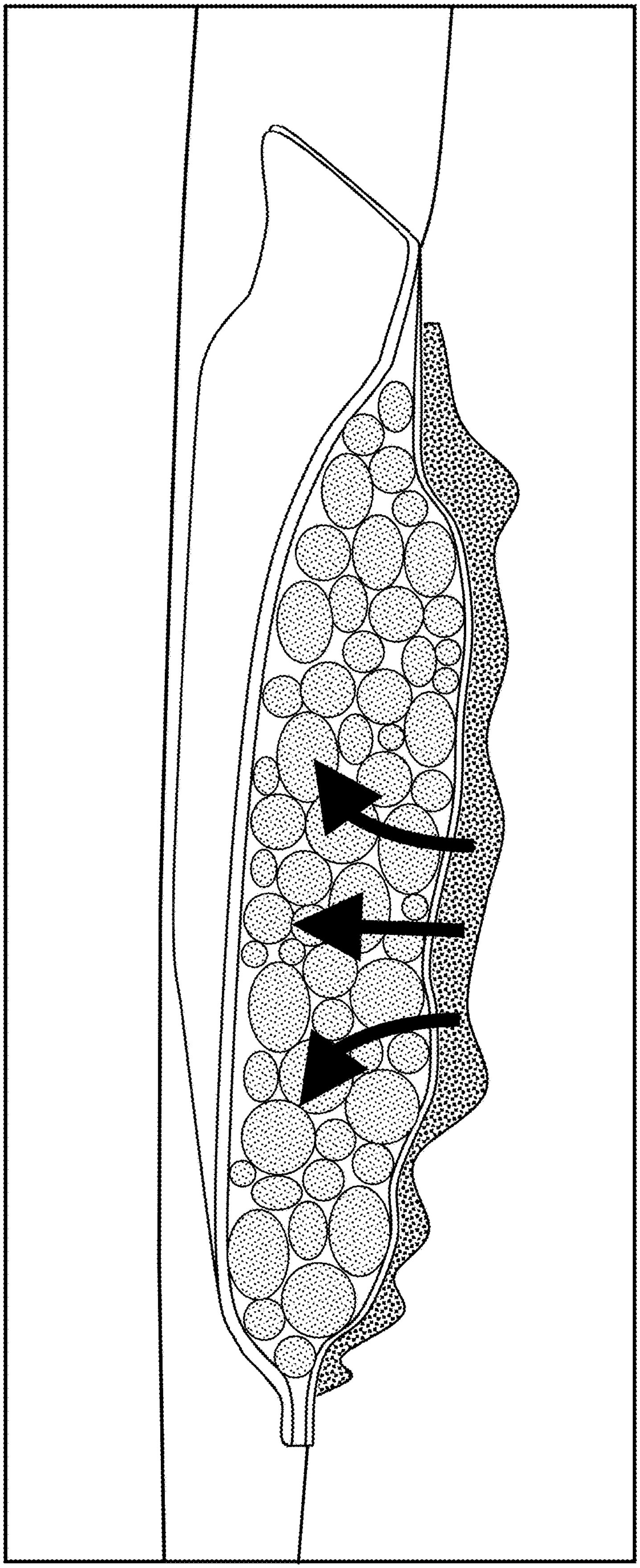
FIG. 2 is a schematic view of the apparatus of FIG. 1 shown in a zoomed-out perspective.

A plurality of the separate and porous ceramic particles is encased in a liquid and gas permeable sachet to form an apparatus for obtaining a biological sample from an exposed surface of a human or animal body (e.g., a wound). For example, see FIG. 1 and FIG. 2. The sachet is a sterile sachet and the separate and porous ceramic particles are packed loosely therein so as to allow air to pervade therethrough. The sachet is formed from an organic, non-woven material.

The plurality of separate and porous ceramic particles has a relatively large surface area and their micro-pores exhibit a significant capillary suction force.

In use, when the apparatus makes contact with the wound of the human or animal body, the plurality of separate and porous ceramic particles exert a capillary suction force on biological material present on the surface of the wound. The biological material is then absorbed, transported and stored in the micro-pores of the plurality of separate and porous ceramic particles. Since each separate and porous ceramic particle is in contact with surrounding particles of the same kind, biological material on the surface of the wound of the human or animal body migrates continuously between the particles to equalize the hydrostatic potential of all the separate and porous ceramic particles in the sachet. There is no driving force for the biological material to leave the micro-pores of the separate and porous ceramic particles. In this manner, a biological sample is obtained from the wound of the human or animal body.

As discussed above, each of the plurality of separate and porous ceramic particles is made from alumina ($Al_2O_3$). The surfaces of the plurality of alumina ($Al_2O_3$) particles are highly charged. The surfaces of the alumina ($Al_2O_3$) particles are relatively rough and have a wetting angle of 0°. Therefore, the alumina particles are easily wetted. The alumina ($Al_2O_3$) particles typically have a surface area of 0.5 $m^2$ per gram of alumina ($Al_2O_3$). Each gram of alumina ($Al_2O_3$) comprises $3.5\times10^{21}$ oxygen ions ($O^{2-}$) and $2.4\times10^{21}$ aluminium ions ($Al^{3+}$), a fair portion of which are exposed to the surface of the particles.

It is known that every cell in a living organism contains an electrical charge defined as the difference between charged atoms on either side of the cell's membrane. A proton colloidal solid, on the other hand, may develop a surface charge due to the ionization of side-chain amino acid groups.

In use, when the plurality of separate and porous alumina particles comes into contact with biological material from the wound, the highly charged alumina surfaces ($5.9\times10^{21}$ ionic charges per gram) are continuously wetted by biological material. The surfaces of the plurality of separate and porous alumina particles are rough and ideal for adsorbing charged colloidal cells, microorganism, biomarkers, deoxyribonucleic acid (DNA) molecules, proteins, and endotoxins and the like to adhere thereto. Adhesion is caused by ionic and electrostatic interactions, hydrogen bonding and charge-transfer interactions. In this manner, strong adsorption takes place and a biological sample is obtained from the wound of the human or animal body.

The biological material includes wound exudate containing any one or more selected from the group consisting of microorganisms, biomarkers, deoxyribonucleic acid (DNA), proteins, cellular molecules, endotoxins or combinations thereof, macrophages, neutrophils, fibroblasts, platelets, cytokines molecules including TNF-α, interleukins (ILs) and growth factors, including platelet-derived growth factor (PDGF), matrix metalloproteinases (MMPs), tissue inhibitors of metalloproteinases (TIMPs), IL-1, IL-6, and MMPs, proteases, protease inhibitors, and inflammatory markers, and the microorganisms include any one or more selected from the group consisting of bacteria, viruses, fungi and parasites.

The apparatus for obtaining a biological sample from an exposed surface (e.g., a wound) of a human or animal body may include an adhesive dressing. When the apparatus is removed from the wound, the biological material siphoned off from the wound locates in the micro-pores as well as on the surfaces of the plurality of separate and porous ceramic particles. This biological material then forms the biological sample obtained from the wound.

The biological sample obtained from the wound is subjected to sonication to disintegrate a biofilm of microorganisms (e.g., bacteria) present in the biological sample and to form a sonication fluid containing microorganisms. Sonication is typically performed at frequencies of 20 kilohertz. The sonication fluid containing microorganisms is then used to cultivate microorganisms for identifying microorganisms present in the sonication fluid containing microorganisms. These microorganisms are typically bacteria and by cultivating the bacteria the different strains of bacteria present in the sonication fluid can be identified. This enables a healthcare practitioner to prescribe the correct treatment for an infected wound of a human or animal patient.

The sonication fluid can also be used to identify biomarkers which are indicative of the stage of wound healing. This will further inform a healthcare practitioner to prescribe the correct treatment for an infected wound of a human or animal patient.

It was found that the biological sample obtained from the wound could be analysed to predict wound healing and to guide wound care. In particular, analysing the levels of macrophages, neutrophils, fibroblasts, platelets, cytokines molecules including TNF-α, interleukins (ILs) and growth factors, including platelet-derived growth factor (PDGF), matrix metalloproteinases (MMPs), tissue inhibitors of metalloproteinases (TIMPs), IL-1, IL-6, and MMPs, proteases, protease inhibitors, and inflammatory markers, provide useful insight to wound care specialists on the status of the wound healing process and assist in predicting progress and prescribing the appropriate treatment regime.

It will be appreciated by those skilled in the art that the invention is not limited to the precise details as described herein and that many variations are possible without departing from the scope of the invention.

The description is presented by way of example only in the cause of providing what is believed to be the most useful and readily understood description of the principles and conceptual aspects of the invention. In this regard, no attempt is made to show more detail than is necessary for a fundamental understanding of the invention. The words which have been used herein are words of description and illustration, rather than words of limitation.

The invention claimed is:

1. An apparatus for obtaining a biological sample from an exposed surface of a human or animal body, the apparatus including a plurality of separate and porous ceramic particles for absorbing and adsorbing biological material from the exposed surface; and a permeable covering for containing the plurality of separate and porous ceramic particles, wherein the biological material having been absorbed and adsorbed by the plurality of separate and porous ceramic particles forms the biological sample;

wherein the plurality of separate and porous ceramic particles have a diameter of between 300 and 3000 micrometers; and wherein the plurality of separate and porous ceramic particles have a charged surface caused by ionic and electrostatic interaction, hydrogen bonding and charge-transfer interactions.

2. The apparatus according to claim 1, wherein the plurality of separate and porous ceramic particles are inert and have a porosity of between 25% and 85%.

3. The apparatus according to claim 1, wherein the plurality of separate and porous ceramic particles have pores with a diameter of between 0.3 and 30 micrometers and wherein the pores are cellular in nature and are interconnected with one another by means of blow-holes.

4. The apparatus according to claim 1, wherein the permeable covering is in a form of a sterile permeable and wettable sachet formed from an organic, non-woven material.

5. The apparatus according to claim 1, wherein the exposed surface is a wound of the human or animal and the biological material includes wound exudate containing any one or more selected from the group consisting of microorganisms, biomarkers, deoxyribonucleic acid (DNA), proteins, cellular molecules, endotoxins or combinations thereof, macrophages, neutrophils, fibroblasts, platelets, cytokines molecules including TNF-$\alpha$, interleukins (ILs) and growth factors, including platelet-derived growth factor (PDGF), matrix metalloproteinases (MMPs), tissue inhibitors of metalloproteinases (TIMPs), IL-1, IL-6, and MMPs, proteases, protease inhibitors, and inflammatory markers, and the microorganisms include any one or more selected from the group consisting of bacteria, viruses, fungi and parasites.

6. A method of obtaining a biological sample from an exposed surface of a human or animal body, the method including the steps of providing an apparatus according to claim 1; and contacting the apparatus with the exposed surface to permit the plurality of separate and porous ceramic particles to absorb and adsorb biological material from the exposed surface, wherein the biological material having been absorbed and adsorbed by the plurality of separate and porous ceramic particles forms the biological sample.

7. The method according to claim 6, wherein the exposed surface is a wound of the human or animal and the biological material includes wound exudate containing any one or more selected from the group consisting of microorganisms, biomarkers, deoxyribonucleic acid (DNA), proteins, cellular molecules, endotoxins or combinations thereof, macrophages, neutrophils, fibroblasts, platelets, cytokines molecules including TNF-$\alpha$, interleukins (ILs) and growth factors, including platelet-derived growth factor (PDGF), matrix metalloproteinases (MMPs), tissue inhibitors of metalloproteinases (TIMPs), IL-1, IL-6, and MMPs, proteases, protease inhibitors, and inflammatory markers, and the microorganisms include any one or more selected from the group consisting of bacteria, viruses, fungi and parasites.

8. A diagnostic method including the steps of providing the apparatus according to claim 1; contacting the apparatus with the exposed surface to permit the plurality of separate and porous ceramic particles to absorb and adsorb biological material from the exposed surface; and subjecting the apparatus to sonication to form a sonication fluid, the sonication step serving to disintegrate a biofilm of microorganisms present in the absorbed and adsorbed biological material so as to form the sonication fluid containing microorganisms.

9. The diagnostic method according to claim 8, wherein the sonication is performed at frequencies of 20 kilohertz.

10. The diagnostic method according to claim 8, which includes an additional step of using the sonication fluid to cultivate a bacterial culture or cultures for identifying bacterial strains present in the sonication fluid.

11. The diagnostic method according to claim 8, wherein the exposed surface is a wound of the human or animal and the biological material includes wound exudate containing any one or more selected from the group consisting of microorganisms, biomarkers, deoxyribonucleic acid (DNA), proteins, cellular molecules, endotoxins or combinations thereof, macrophages, neutrophils, fibroblasts, platelets, cytokines molecules including TNF-$\alpha$, interleukins (ILs) and growth factors, including platelet-derived growth factor (PDGF), matrix metalloproteinases (MMPs), tissue inhibitors of metalloproteinases (TIMPs), IL-1, IL-6, and MMPs, proteases, protease inhibitors, and inflammatory markers, and the microorganisms include any one or more selected from the group consisting of bacteria, viruses, fungi and parasites.

* * * * *